United States Patent [19]

Hara et al.

[11] 4,246,329

[45] Jan. 20, 1981

[54] METHOD FOR IMPROVING THE LIGHT FASTNESS OF ORGANIC SUBSTRATE MATERIALS INCLUDING PHOTOGRAPHIC DYE IMAGES

[75] Inventors: Hiroshi Hara, Asaka; Kotaro Nakamura; Yoshiaki Suzuki, both of Minami-ashigara, all of Japan

[73] Assignee: Fuji Photo Film Co., Ltd., Minami-ashigara, Japan

[21] Appl. No.: 969,520

[22] Filed: Dec. 14, 1978

[30] Foreign Application Priority Data

Dec. 14, 1977 [JP] Japan ................................ 52/150345

[51] Int. Cl.[3] ........................ G03C 1/40; G03C 1/84; G03C 7/00; G03C 1/10

[52] U.S. Cl. .......................................... 430/17; 8/476; 8/490; 260/45.75 C; 260/45.75 M; 260/45.75 N; 260/45.75 R; 428/411; 428/500; 428/539; 430/216; 430/372; 430/512; 430/517; 430/551; 430/559; 430/561

[58] Field of Search .............. 96/56, 77, 84 R, 840 V, 96/100, 99, 119 R; 260/47.75 C, 45.75 M, 45.75 R, 45.75 N; 423/366; 8/4, 74; 428/539, 500, 411, 8, 423, 260; 430/17, 216, 372, 512, 517, 551, 559, 561

[56] References Cited

U.S. PATENT DOCUMENTS

| | | | |
|---|---|---|---|
| 2,615,860 | 10/1952 | Burgess ........................ | 260/45.75 N |
| 4,050,938 | 9/1977 | Smith et al. ........................ | 96/84 R |

*Primary Examiner*—Richard L. Schilling

*Attorney, Agent, or Firm*—Sughrue, Rothwell, Mion, Zinn and Macpeak

[57] ABSTRACT

The light stability of organic dyes is improved by the presence of at least one of the complexes represented by general formula (I) or (II)

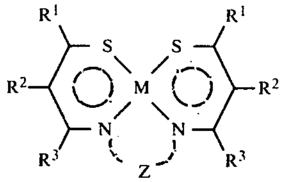

(I)

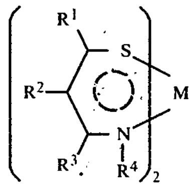

(II)

wherein M represents a Cu, Co, Ni, Pd or Pt atom; $R^1$ and $R^4$, which may be the same or different, each represents an alkyl group or an aryl group; $R^2$ and $R^3$, which may be the same or different, each represents a hydrogen atom, an alkyl group or an aryl group; or $R^1$ and $R^2$, and $R^3$ and $R^4$ may combine to represent a non-metallic atomic group necessary to form a 6-membered ring; and Z represents a non-metallic atomic group necessary to form a 5-membered ring, 6-membered ring, 8-membered ring, or 10-membered ring.

16 Claims, No Drawings

METHOD FOR IMPROVING THE LIGHT FASTNESS OF ORGANIC SUBSTRATE MATERIALS INCLUDING PHOTOGRAPHIC DYE IMAGES

BACKGROUND OF THE INVENTION

1. Field of the Invention

This invention relates to a light stabilization method for organic substrate materials and, more particularly, it relates to a method of stabilizing organic compounds, in particular, organic dyes to light.

2. Description of the Prior Art

In general, it is widely known that organic substrate materials such as organic dyes tend to fade or discolor by the action of light, and in the field of inks, textile dyeing, or color photography, various studies for preventing fading or discoloring of such organic dyes, that is, for improving the light fastness of these organic dyes have been made. This invention is used very advantageously for improving the light fastness or light stability of these organic substrate materials.

The term "substrate materials" or "substrate materials" as employed in this specification include materials which are colored or colorless to the human eye under sunlight and also include materials having simply an absorption maximum in the visible region, such as, for example, optical whitening agents, as well as the materials having the absorption maximum in an infrared region. Furthermore, the organic substrate materials which are the object of this invention include organic materials having their absorption maximum of about 300 nm in the ultraviolet region to about 800 nm in the infrared region. These organic substrate materials occur particularly in photographic materials, e.g., color films, prints, diffusion transfer units, etc., in colored polymers useful as agricultural vinyl cover sheets, umbrellas, tents, etc.; fluorescent whitening agent; and dyed textiles, etc., and this invention is directed to improving the light fastness of these materials in each of these environments.

The term "dyestuff" or "dyes" as used in this specification include organic materials which are viewed by the human eye as colored materials under sunlight.

The term "light" used in this specification means electromagnetic radiation having a wavelength of shorter than about 800 nm and includes ultraviolet rays having wavelengths of shorter than about 400 nm, visible rays having wavelengths of from about 400 nm to about 700 nm, and infrared rays having wavelengths of from about 700 nm to about 800 nm.

Hitherto, it is well known that organic substrate materials such as coloring matters or dyes have a tendency to fade or discolor under the action of light and many methods have been reported for reducing the fading or discoloring tendency of these organic materials, that is, methods of improving the light fastness of the organic substrate materials. For example, U.S. Pat. No. 3,432,300 discloses that the light fastness of organic compounds such as indophenol, indoaniline, azo and azomethine dyes to visible and ultraviolet light is improved by mixing therewith a phenol-type compound having a fused heterocyclic ring system.

In general, azomethine dyes or indoaniline dyes are formed by the reaction of oxidized aromatic primary amino developing agent and color photographic couplers and various methods for improving the stability of photographic images, i.e., color images are known in the field of silver halide photographic materials as described in Chapter 17 of C. E. K. Mees and T. H. James, *The Theory of the Photographic Process*, published in 1967 by Macmillan Co. For example, it is known the hydroquinone derivatives as described in U.S. Pat. Nos. 2,360,290, 2,418,613, 2,675,314, 2,701,197, 2,704,713, 2,728,659, 2,732,300, 2,735,765, 2,710,801 and 2,816,028 and British Pat. No. 1,363,921, the gallic acid derivatives as described in U.S. Pat. Nos. 3,457,079 and 3,069,262 and Japanese Patent Publication No. 13,496/68, the p-alkoxyphenols as described in U.S. Pat. Nos. 2,735,765 and 3,698,909, and the derivatives such as chroman and cumarone as described in U.S. Pat. Nos. 3,432,300, 3,573,050, 3,574,627, 3,764,337, 3,574,626, 3,698,909 and 4,015,990. However, while these compounds may have some effect as a fade preventing agent or discoloration preventing agent for color images, the effect is not sufficient.

Also, a method for improving the light stability of the organic substrate compounds using an azomethine quenching compound of which the absorption maximum is higher than the absorption maximum of the substrate material is described in British Pat. No. 1,451,000 but, since the azomethine quenching compound itself is strongly colored, the use of such a compound is disadvantageous in the point that it greatly influences the color hue of the substrate compounds.

Furthermore, in J. P. Guillory and R. S. Becker, *J. Polym. Sci.*, Polym. Chem. Ed., 12, 993 (1974) and R. P. R. Ranaweera and G. Scott, *J. Polym. Sci., Polym. Lett. Ed.*, 13, 71 (1975), the use of metal complexes for preventing the light deterioration of polymer is reported. Other stabilization methods of dyes by metal complexes are described in Japanese Patent Application (OPI) No. 87,649/75 (The term "OPI" as used herein refers to a "published unexamined Japanese patent application") and Research Disclosure 15162 (1976). However, since the fade prevention effect of these complexes is not so high and the solubility of these complexes in organic solvents is low, it is difficult to add a sufficient amount of the complexes to obtain the desired fade prevention effect of them. Moreover, since these complexes themselves are greatly colored, these complexes suffer the disadvantage that if they are added in a large amount, they badly influence the purity and color hue of the organic substrate material, in particular dyes.

Furthermore, good fade preventing agents for cyan dyes have not been known.

SUMMARY OF THE INVENTION

An object of this invention is, therefore, to provide a method of improving the light stability of organic substrate materials.

Another object of this invention is to provide a method of improving the light stability of organic substrate materials without degrading the color hue and purity of the organic substrates and, particularly, without degrading the color hue and purity of dyes.

Still another object of this invention is to provide a method of improving the light stability of organic substrate materials using a stabilizing agent having a high solubility in organic solvent and high miscibility with the organic substrate materials.

A further object of this invention is to provide a method of improving the light stability of color images forming color photographic images.

Another object of this invention is to provide a method of improving the light stability of dyes formed by the reaction of an oxidized aromatic primary amino developing agent and color couplers.

Still another object of this invention is to improve the light fastness of colored polymers useful as agricultural vinyl sheets, umbrellas, tents, etc.

Other objects of this invention will become apparent from the following description of the invention.

DESCRIPTION OF THE INVENTION

The above-described objects and other objects of this invention can be attained by allowing at least one of the compounds represented by the following general formula (I) or (II) to coexist together with the organic substrate materials having the absorption maximum in the range of from about 300 nm to about 800 nm:

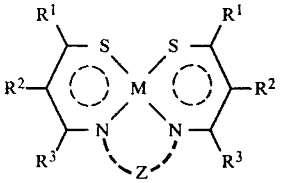

(I)

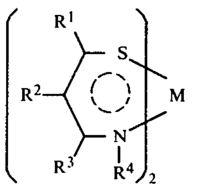

(II)

wherein M represents a Cu, Co, Ni, Pd or Pt atom; $R^1$ and $R^4$, which may be the same or different, each represents an alkyl group or an aryl group; $R^2$ and $R^3$, which may be the same or different, each represents hydrogen atom, an alkyl group, or an aryl group; or $R^1$ and $R^2$, and $R^3$ and $R^4$ may combine to form the non-metallic atomic group necessary to complete a 6-membered ring; and Z represents the non-metallic atomic group necessary to complete a 5-membered ring, a 6-membered ring, an 8-membered ring, or a 10-membered ring.

The terms "in the presence of" or "coexistant with" as used in the specification refer not only to coexistence of the substrate material and the compound of the formula (I) in the same solution, dispersion, emulsion or layer but also to the existence of the organic substrate and the complex in, for example, adjacent layers of a multi-layered photographic material. As long as the complex compound is associated with the organic substrate material such that it improves the light fastness of the organic substrate, it is used "in the presence of" or "coexists" with the substrate for purposes of the present invention.

The alkyl groups represented by $R^1$, $R^2$, $R^3$ and $R^4$ in the above-described general formulae include substituted and unsubstituted alkyl group, the preferred carbon number of the alkyl group excluding the carbon atoms of any substituent is from 1 to 20. The alkyl group may be a straight chain alkyl group or a branched alkyl group. Examples of the alkyl group are a methyl group, an ethyl group, a propyl group, a butyl group, an amyl group, a hexyl group, an octyl group, a decyl group, a hexadecyl group, a heptadecyl group, an octadecyl group, etc.

The aryl groups represented by $R^1$, $R^2$, $R^3$ and $R^4$ in the above-described general formulae include substituted and unsubstituted mono or bicyclic aryl groups. The preferred carbon number of the aryl group excluding the carbon atoms of any substituent is from 6 to 14. Examples of the aryl group include a phenyl group and a naphthyl group.

The 6-membered ring formed by combining $R^1$ and $R^2$ with each other includes a 6-membered ring condensed with another ring or nucleus and includes both a substituted 6-membered ring and unsubstituted 6-membered ring. These 6-membered rings include aromatic rings, for example, a benzene ring and a naphthalene ring.

The 6-membered ring formed by combining $R^3$ and $R^4$ with each other includes a 6-membered ring which may be condensed with another ring and further includes both a substituted 6-membered ring and unsubstituted 6-membered ring. These 6-membered rings include, for example, a pyridine ring and a quinoline ring.

The non-metallic atomic groups represented by Z necessary for forming a 5-membered ring, a 6-membered ring, an 8-membered ring or a 10-membered ring include the non-metallic atomic groups represented by the following formulae (a), (b) or (c):

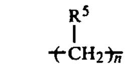

(a)

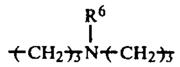

(b)

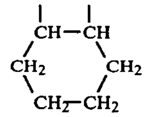

(c)

wherein n represents 2 or 3 and $R^5$ and $R^6$ represent a hydrogen atom, an alkyl group or an aryl group. Of these, a 5-, 6- or 10-membered ring is preferred.

The alkyl groups represented by $R^5$ and $R^6$ in the above formulae include substituted and unsubstituted alkyl groups. The preferred carbon number of the alkyl group excluding the carbon atoms of any substituent is 1 to 20. These alkyl groups may be straight chain alkyl groups or branched alkyl groups. Practical examples of these alkyl groups include the ones illustrated above with regard to $R^1$, $R^2$, $R^3$ and $R^4$.

The aryl groups represented by $R^5$ and $R^6$ in the above formula include both a substituted and unsubstituted aryl groups and the preferred carbon number of the aryl group excluding the carbon atoms of any substituent is 6 to 14. Practical examples of these aryl groups include the same ones as illustrated with respect to $R^1$, $R^2$, $R^3$ and $R^4$.

The above-described alkyl group and aryl group represented by $R^1$, $R^2$, $R^3$, $R^4$ and $R^5$, the above-described 6-membered ring formed by $R^1$ and $R^2$ or by $R^3$ and $R^4$, and the above-described 5-membered ring, 6-membered ring, 8-membered ring and 10-membered ring represented by Z may substituted by, for example, a halogen atom (e.g., chlorine atom, bromine atom, fluorine atom, etc.), a cyano group, a straight chain or branched chain alkyl group containing 1 to 20 carbon atoms (e.g., methyl group, ethyl group, propyl group, butyl group, hexyl group, octyl group, decyl group, dodecyl group, tetradecyl group, hexadecyl group, hetadecyl group, octadecyl group, methoxyethoxyethyl group, etc.), a monocyclic or bicyclic aryl group containing 6 to 14 carbon atoms excluding the carbon atoms in any substituent moiety (e.g., phenyl group, tolyl group, naphthyl group, chlorophenyl group, methoxyphenyl group, acetylphenyl group, etc.), an acyloxy group (e.g., an acetoxy group, a benzoyloxy group, a p-methoxybenzoyloxy group, etc.), an alkoxy group (e.g., a methoxy group, an ethoxy group, a butoxy group, a propoxy group, a methoxyethoxy group, etc.), an aryloxy group (e.g., a phenoxy group, a tolyloxy group, a naphthoxy group, a methoxyphenoxy group, etc.), an aralkyl group (e.g., a benzyl group, a phenethyl group, an anisyl group, etc.), an alkoxycarbonyl group (e.g., a methoxycarbonyl group, a butoxycarbonyl group, a phenoxycarbonyl group, etc.), an aryloxycarbonyl group (e.g., a phenoxycarbonyl group, a tolyloxycarbonyl group, a methoxyphenoxycarbonyl group, etc.), an acyl group (e.g., a formyl group, an acetyl group, a valeryl group, a stearoyl group, a benzoyl group, a toluoyl group, a naphthoyl group, a p-methoxybenzoyl group, etc.), an acyloxy group (e.g., acetoxy, benzyloxy, toluyloxy, naphthoyloxy, etc.), an acylamino group (e.g., an acetamido group, a benzamido group, a methoxyacetamido group, etc.), an anilino group (e.g., a phenylamino group, an N-methylanilino group, an N-phenylanilino group, an N-acetylanilino group, etc.), an alkylamino group (e.g., an n-butylamino group, an N,N-diethylamino group, a 4-methoxy-n-butylamino group, etc.), a carbamoyl group (e.g., an n-butylcarbamoyl group, an N-(4-methoxy-n-butyl)carbamoyl group, etc.), a sulfamoyl group (e.g., an n-butylsulfamoyl group, an N,N-diethylsulfamoyl group, an n-dodecylsulfamoyl group, an N-(4-methoxy-n-butyl)-sulfamoyl group, etc.), a sulfonylamino group (e.g., a methylsulfonylamino group, a phenylsulfonylamino group, a methoxymethylsulfonylamino group, etc.), or a sulfonyl group (e.g., a mesyl group, a tosyl group, a methoxymethanesulfonyl group, etc.). In the above substituents, the alkyl moieties may be straight or branched chain and contain 1 to 20 carbon atoms. The aryl moieties may be monocyclic or bicyclic and contain 6 to 14 carbon atoms.

In the compounds represented by the general formula (I) or (II), the preferred compounds in this invention are represented by the following general formula (I-A) or (II-A):

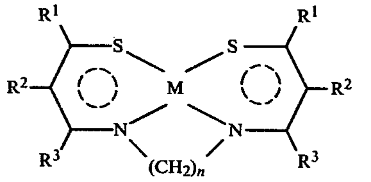

(I-A)

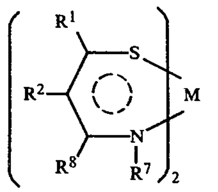

(II-A)

wherein M represents a Cu, Co, Ni, Pd, or Pt atom; $R^1$ and $R^7$ each represents an alkyl group or an aryl group; $R^2$, $R^3$ and $R^8$ each represents a hydrogen atom, an alkyl group, or an aryl group, or $R^1$ and $R^2$ may combine to form a non-metallic atomic group necessary to complete a 6-membered ring; and n represents 2 or 3.

As the alkyl group or the aryl group represented by $R^1$, $R^2$, $R^3$, $R^7$ and $R^8$ in the general formula (I-A) and the general formula (II-A), the alkyl group or the aryl groups illustrated and defined in relation to the general formula (I) and the general formula (II) can be preferably used. Also, as the 6-membered ring formed by $R^1$ and $R^2$ in general formulae (I-A) and (II-A), the 6-membered ring defined in relation to the general formula (I) and the general formula (II) can be preferably used. Also, as the substituents for the groups represented by $R^1$, $R^2$, $R^3$, $R^7$ and $R^8$ in general formulae (I-A) and (II-A), the substituents for the groups represented by $R^1$, $R^2$, $R^3$, $R^4$, $R^5$ and $R^6$ in the general formulae can be preferably used.

Furthermore, in the compounds represented by the general formula (I-A) or the general formula (II-A), the compounds wherein M is a Cu, Co or Ni atom are particularly preferred for use in this invention.

The following structural formulae are metal complexes within the scope of the general formula (I) and the general formula (II) but they are only illustrations of compounds which are particularly effective in the practice of this invention and this invention is not limited to the use of these compounds.

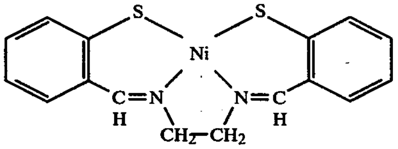

I-1

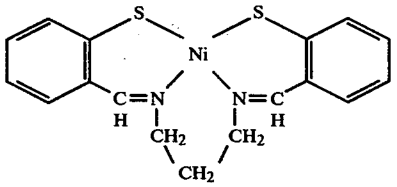

I-2

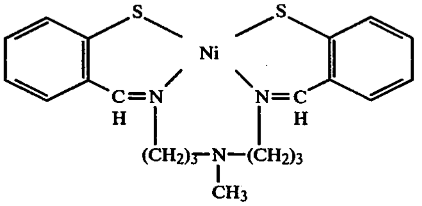

I-3

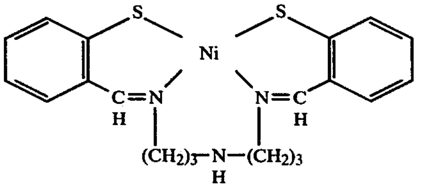

I-4

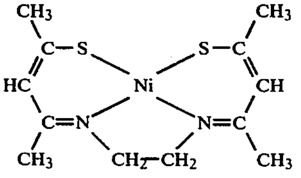

I-5

-continued
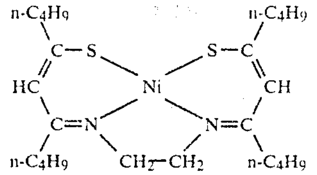
I-6
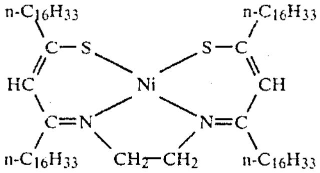
I-7
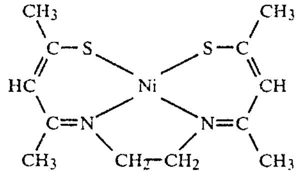
I-8
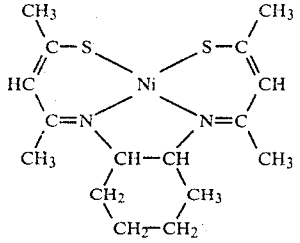
I-9
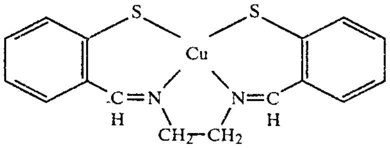
I-10
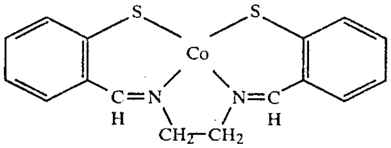
I-11
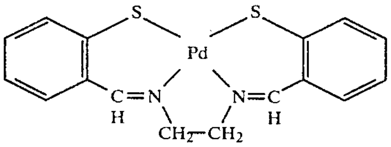
I-12
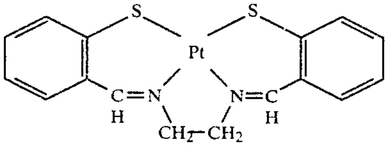
I-13
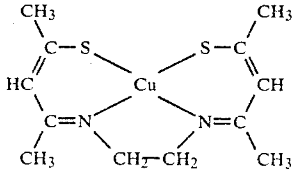
I-14
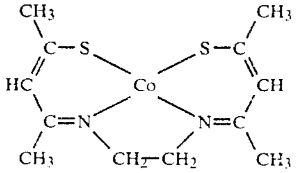
I-15
-continued
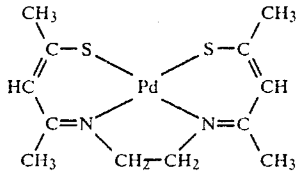
I-16
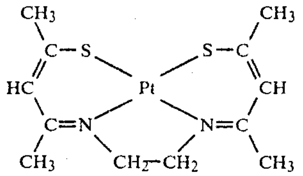
I-17
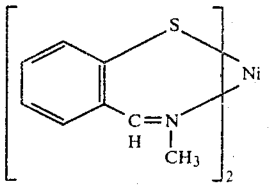
II-1
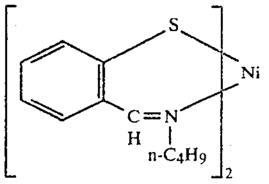
II-2
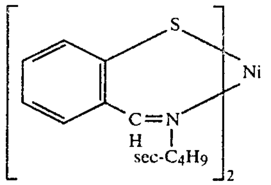
II-3
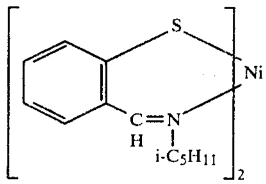
II-4
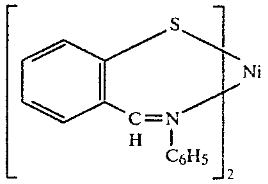
II-5
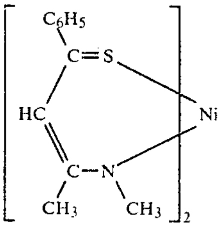
II-6

-continued
II-7
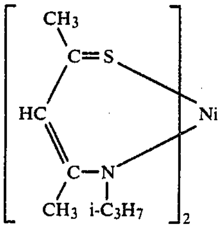
II-8
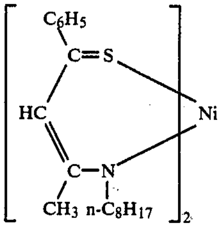
II-9
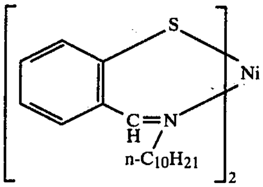
II-10
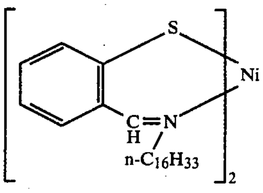
II-11
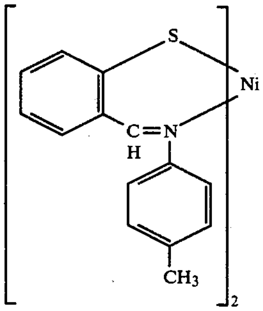
II-12
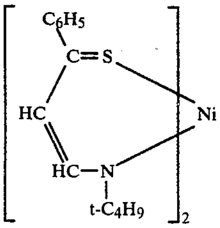
II-13
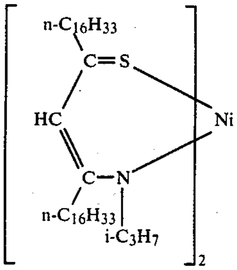
-continued
II-14
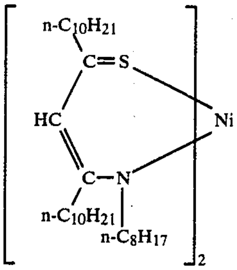
II-15
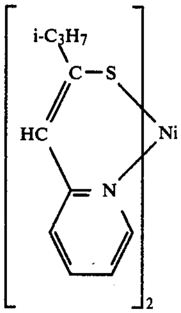
II-16
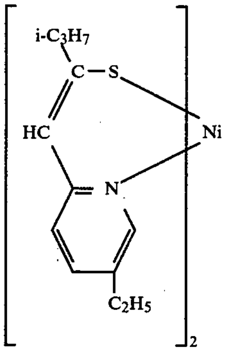
II-17
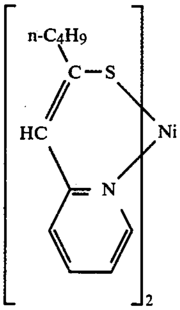
II-18
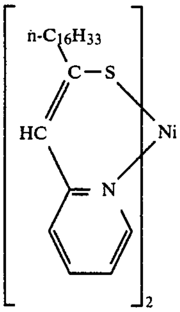

-continued
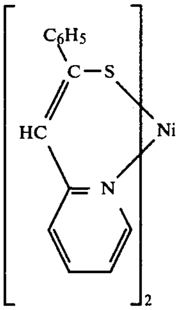
II-19
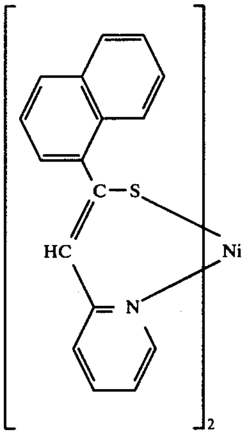
II-20
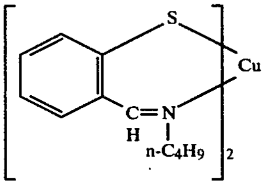
II-21
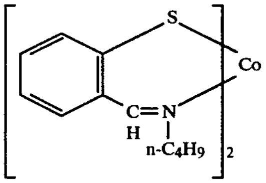
II-22
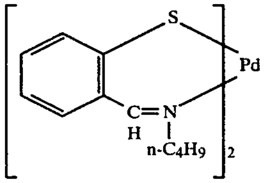
II-23
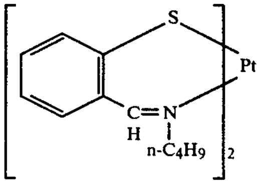
II-24
-continued
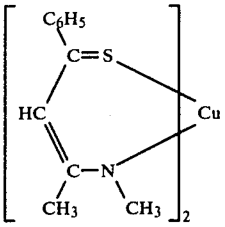
II-25
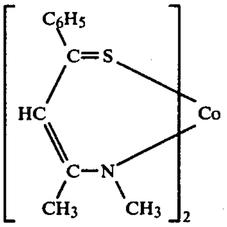
II-26
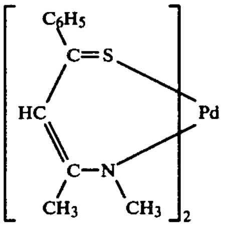
II-27
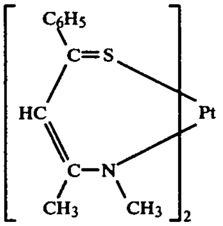
II-28
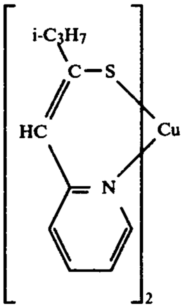
II-29
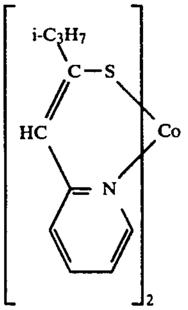
II-30

-continued

II-31

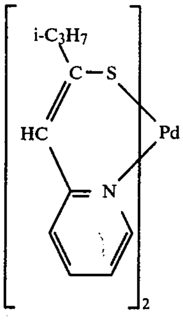

II-32

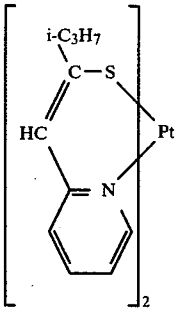

General processes for producing the above mentioned complexes are described in, for example, E. Hoyer and B. Lorenz, *Z. Chem.*, 8, 28 (1968); E. Uhlemann and J. Prakt, *Chem.*, 21, 277 (1963); and I. Bertini, L. Sacconi, and G. P. Speroni, *Inorg. Chem.*, 11, 1323 (1972). Other complexes than those described in the above technical reports may be prepared by the following processes. Ketoamines obtained by the reaction of diketones and amines are reacted with NaSH to produce thioketoamines. A methanol solution of the so obtained various thioketoamine ligands is mixed with a methanol solution of nickel acetate. The resulting mixture is refluxed for an hour. After allowing to cool, the precipitates of the complex are separated and recrystallized, if necessary, in a conventional manner.

SYNTHESIS EXAMPLE 1

Synthesis of Compound I-5

To a solution prepared by dissolving 11.20 g of bisacetylacetone ethylenediimine in 100 ml of methylene chloride was added dropwise a solution of 19 g of $[(C_2H_5)_3O]$ $[BF_4]$ in 50 ml of methylene chloride with stirring at room temperature in nitrogen atmosphere over a period of 15 minutes and, thereafter, the mixture was further stirred for 30 minutes. Then, a suspension of 10 g of NaHS in 100 ml of absolute ethanol was added thereto at room temperature and the resultant mixture was further stirred for one hour at room temperature. The mixture was filtered and the solvent was distilled off from the filtrate to provide a solid, which was recrystallized twice with a mixture of acetone and water. Thus, 7 g of N,N'-ethylenebis(monothioacetylacetoneimine) was obtained. Then, 2.5 g of N,N'-ethylenebis(-monothioacetylacetoneimine was added to a solution of 2.5 g of nickel acetate tetrahydrate in 100 ml of methanol at room temperature and the mixture was further heated on a steam bath for 30 minutes. The reaction mixture obtained was allowed to stand overnight in a refrigerator. The crude crystals of the complex I-5 thus-formed were recrystallized from acetone.

SYNTHESIS EXAMPLE 2

Synthesis of Compound II-7

To a solution of 11.6 g of 1-phenyl-3-monoisopropylamino-2-butene in 100 ml of methylene chloride was added dropwise a solution of 10 g of $[(C_2H_5)_3O]$ $[BF_4]$ in 50 ml of methylene chloride with stirring at room temperature. Thereafter, the mixture was further stirred for 20 minutes and a suspension of 3 g of NaHS in 30 ml of absolute ethanol was added to the mixture. The resultant mixture was further stirred for 15 minutes and filtered. Then, the solvent was distilled off from the filtrate and the solid obtained was recrystallized from n-heptane. Thereafter, 4.4 g of 1-phenyl-3-monoisopropyl-2-butene-1-thione thus-obtained was dissolved in 50 g of t-butyl alcohol and then 2.5 g of nickel acetate tetrahydrate was added to the solution. After heating the mixture on a steam bath for 30 minutes, t-butyl alcohol was distilled off and the solid obtained was recrystallized from hot heptane.

As will be apparent from the extensive discussion and examples of the organic substrate which follows, the present invention is effective with a very wide variety of organic materials, the essential point being that the substrate materials have a maximum absorption wavelength in the range of 300 to 800 nm.

The organic substrate materials in this invention include all dyes belongint to the following classes based on dyeing property, i.e., water-soluble dyes such as basic dyes, acid dyes, direct dyes, soluble vat dyes, mordant dyes, etc.; water-insoluble dyes such as sulfur dyes, vat dyes, oil colors, disperse dyes, azoic dyes, acid dyes, etc.; and reactive dyes. These organic substrate materials include not only the dyes which are seen as colored materials under sunlight but also colorless or light yellow optical whitening dyes.

Of these dyes, the dyes preferably used in conjunction with this invention are quinoneimine dyes (e.g., azine dyes, oxazine dyes, thiazine dyes, etc.), methine and polymethine dyes (e.g., cyanine dyes, azomethine dyes, etc.), azo dyes, anthraquinone dyes, indoamine dyes, indophenol dyes, indigoid dyes, carbonium dyes, formazan dyes, etc., classified by chemical structure.

The organic substrate materials in this invention also include image-forming dyes used in the filed of photography, for example, the dyes formed from color couplers, DRR compounds, DDR couplers, amidrazone compounds, dye developers, etc., and dyes for the silver dye bleach process.

Preferred organic substrate materials in this invention are anthraquinone dyes, quinoneimine dyes, azo dyes, methine dyes, polymethine dyes, indoamine dyes, indophenol dyes, and formazan dyes.

Furthermore, examples of the most preferred dyes used at the practice of this invention are methine dyes, polymethine dyes, indoamine dyes and indophenol dyes. The methine dyes, polymethine dyes, indoamine dyes, and indophenol dyes also include compounds having the following moiety

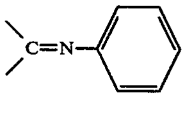

wherein the phenyl group may be substituted by an alkyl group, an alkoxy group, a halogen atom, or an amino group.

The dye-forming couplers suitably used in this invention include yellow dye-forming couplers, magenta dye-forming couplers and cyan dye-forming couplers. These couplers may be so-called 4-equivalent couplers or 2-equivalent couplers as described in U.S. Pat. Nos. 3,277,155 and 3,458,315.

The yellow dye-forming couplers generally contain at least one methylene group activated by carbonyl group (for example, open chain type ketomethylene group) and include β-diketones and β-ketoacylamides such as, for example, benzylacetanilide and α-pivalylacetanilide. Examples of the suitable yellow couplers used in this invention are described in U.S. Pat. Nos. 2,428,054, 4,026,706, 2,499,966, 2,453,661, 2,778,658, 2,908,573, 3,227,550, 3,253,924, 3,277,155 and 3,384,657 and British Pat. No. 503,752.

As the magenta dye-forming couplers used in this invention, there are, for example, 5-pyrazolone type couplers. The couplers of this type are described in, for example, U.S. Pat. Nos. 2,600,788, 2,725,292, 2,908,573, 3,006,759, 3,062,653, 3,152,896, 3,227,550, 3,252,924, 4,026,706 and 3,311,476.

Other magenta dye-forming couplers used in this invention are the indazolones of the type as described in Vittum and Weissberger, *Journal of Photographic Science*, Vol. 6, page 158 et seq. (1958) and practical examples of such magenta dye-forming couplers are pyrazolinobenzimidazole as described in U.S. Pat. No. 3,061,432, pyrazolo-s-triazole as described in Belgian Pat. No. 724,427, and 2-cyanoacetylcumarone as described in U.S. Pat. No. 2,115,394.

The cyan dye-forming couplers which can be used in this invention include phenol compounds and α-naphthol compounds. The compounds of this type are illustrated in U.S. Pat. Nos. 2,275,292, 2,423,730, 2,474,293, 2,895,826, 2,908,573, 3,043,892, 4,026,706, 3,227,550 and 3,253,294.

In general, the couplers described above are further described in, for example, Kirk-Othmer, *Encyclopedia of Chemical Technology*, Vol. 5, pages 822-825 and Glafkides, *Photographic Chemistry*, Vol. 2, pages 596-614.

As described above, when such couplers are used in the practice of this invention, dyes are formed by the reaction of these couplers and an oxidized aromatic primary amino silver halide developing agent.

The developing agent described above includes an aminophenol and a phenylenediamine and they may include a mixture of them.

Typical examples of the developing agent which can form the organic substrate materials by combining various couplers are illustrated as follows:

A

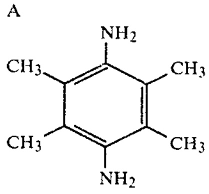

B

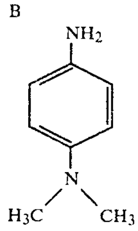

C

-continued

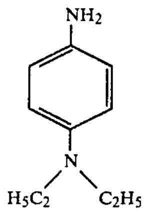

D

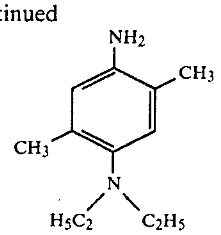

E

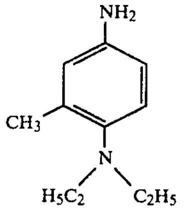

F

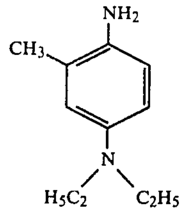

G

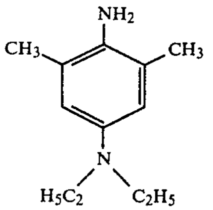

H

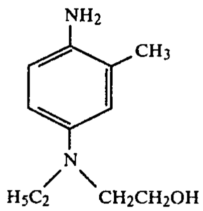

I

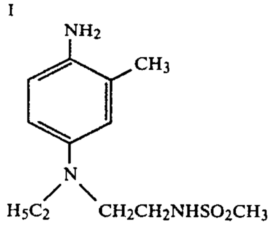

J

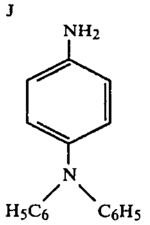

K

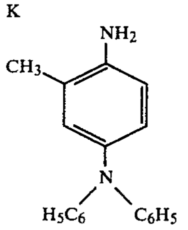

L

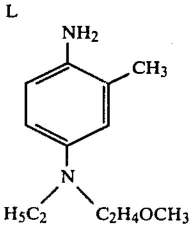

The developing agents illustrated above and others can provide organic substrates upon the reaction with photographic color couplers. Cyan, magenta and yellow couplers which are preferably employed are represented by the formulae (IIIa), (IIIb) or (IIIc) below, respectively:

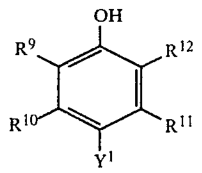

(IIIa)

wherein $R^9$, $R^{10}$, $R^{11}$ and $R^{12}$ each represents a hydrogen atom, a halogen atom (e.g., fluorine, chlorine, bromine or iodine), an alkyl group having 1 to 20 carbon atoms (hereafter, all of the alkyl groups referred to with respect of formulae (IIIa), (IIIb) and (IIIc) may possess 1 to 20 carbon atoms) (e.g., methyl, ethyl, octyl, dodecyl, tetradecyl, octadecyl, etc.); an alkyl- or aryl-substituted carbamoyl wherein the aryl moiety has 6 to 10 carbon atoms, (hereafter, all of the aryl groups referred to with respect of formulae (IIIa), (IIIb) and (IIIc) may possess 6 to 10 carbon atoms) (e.g., methylcarbamoyl, ethylcarbamoyl, dodecylcarbamoyl, tetradecylcarbamoyl, octadecylcarbamoyl, N-phenylcarbamonyl, N-tolylcarbamoyl, etc.); an alkyl- or aryl-substituted sulfamoyl group (e.g., methylsulfamoyl, ethylsulfamoyl, dodecylsulfamoyl, tetradecylsulfamoyl, octadecylsulfamoyl, N-phenylsulfamoyl, N-tolylsulfamoyl, etc.); an alkyl- or aryl-substituted amido group (e.g., acetamido, butylamido, benzamido, phenacetamido, etc.); a sulfonamido group (e.g., benzenesulfonamido), a phosphoric acid amido group, a ureido group, etc.

$R^9$ and $R^{10}$ may combine with each other to form a 6-membered carbocylic ring (e.g., a benzene ring which may further be substituted with an alkyl or aryl group).

$Y^1$ represents a hydrogen atom, a halogen atom (e.g., fluorine, chlorine, bromine or iodine); or a group which is releasable upon the reaction with the oxidation product of a developing agent (e.g., an alkoxy group wherein the alkyl moiety has 1 to 20 carbon atoms; an aryloxy group wherein the aryl moiety has 6 to 10 carbon atoms; a sulfonamido group, a sulfonyl group, a carbamoyl group, an imido group, an amino-sulfonyloxy group, an alkylcarbonyloxy group, an arylcarbonyloxy group, an alkylthio group, an arylthio group, a heterocyclic ring thio group, etc.; the details of which are well known in the art.

The alkyl, carbamoyl, sulfamoyl and amido groups expressed by $R^9$, $R^{10}$, $R^{11}$ and $R^{12}$, or the 6-membered ring formed by combining $R^9$ and $R^{10}$ with each other can also be substituted with other substituents, for example, an alkyl group (e.g., methyl, ethyl, propyl, octyl, dodecyl, tetradecyl, octadecyl, etc.); an aryl group (e.g., phenyl, tolyl, naphthyl, etc.); an aryloxy group, (e.g., phenoxy, 2,5-di(t)-amylphenoxy, etc.); a halogen atom (e.g., chlorine, bromine, fluorine, etc.); and the like.

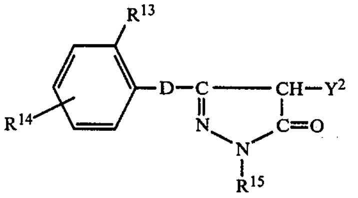
(IIIb)

wherein $R^{13}$ represents a hydrogen atom, a halogen atom (e.g., chlorine, bromine, fluorine, etc.); an alkyl group (e.g., methyl, ethyl, n-propyl, etc.); or an alkoxy group (e.g., methoxy, ethoxy, etc.); $R^{14}$ represents an alkyl group (e.g., methyl, ethyl, octyl, dodecyl, tetradecyl, octadecyl, etc.); an amido group (e.g., butanamido, decanamido, tetradecanamido, nonadecanamido, etc.); an imido group (e.g., tetradecylsuccinimido, octadecylsuccinimido, etc.); an N-alkylcarbamoyl group (e.g., decylcarbamoyl, tetradecylcarbamoyl, octadecylcarbamoyl, etc.); an N-alkylsulfamoyl group (e.g., decylsulfamoyl, tetradecylsulfamoyl, octadecylsulfamoyl, etc.); an alkoxycarbonyl group (e.g., decyloxycarbonyl, tetradecyloxycarbonyl, octadecyloxycarbonyl, etc.); an acyloxy group (e.g., valeryloxy, palmitoyloxy, stearoyloxy, oleyloxy, benzoyloxy, toluoyloxy, etc.); a sulfonamido group, a urethane group, etc., and $R^{15}$ represents an aryl group (e.g., phenyl, naphthyl, etc.), said alkyl and aryl groups having the number of carbon atoms discussed above with respect to formula (IIIa).

D represents an amino group, a carbonylamino group, or a ureido group.

$Y^2$ represents a hydrogen atom, a halogen atom (e.g. chlorine, bromine, etc.); or a group which is releasable upon reaction with the oxidation product with a developing agent (e.g., an arylazo group, an aryloxy group, an acyloxy group, an alkylthio group, an arylthio group, etc.). Such groups are well known.

The alkyl or alkoxy group represented by $R^{13}$, the alkyl, amido, N-alkylcarbamoyl, N-alkylsulfamoyl, alkoxycarbonyl or acyloxy group represented by $R^{14}$, or the aryl group represented by $R^{15}$ can also be substituted with other substituents, for example, an alkyl group, an aryl group, an alkoxy group, an aryloxy group, an amido group, an N-alkylcarbamoyl group, an N-alkylsulfamoyl group, an acyloxy group, a carboxy group, a sulfo group, a halogen atom (e.g., chlorine, bromine, fluorine, etc.), or the like.

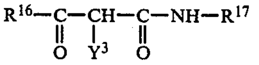
(IIIc)

wherein $R^{16}$ represents an alkyl group (e.g., methyl, ethyl, (t)-butyl, (t)-octyl, etc.) or an aryl group (e.g., phenyl) and $R^{17}$ represents an aryl group (e.g., phenyl).

$Y^3$ represents a hydrogen atom, a halogen atom (e.g., chlorine, bromine, etc.), or a group which is releasable upon reaction with the oxidation product of a developing agent, for example, a heterocyclic nuclei (e.g., naphthoimido, succinimido, 5,5-dimethylhydantoinyl, 2,4-oxazolidinedione residue, imido, pyridone residue, pyridazone residue, etc.), an acyloxy group, a sulfonyloxy group, an aryloxy group, a ureido group; which are well known in the art.

The alkyl or aryl group represented by $R^{16}$ and the aryl group represented by $R^{17}$ can also be substituted with other substituents, for example, an alkyl group, an aryl group, an alkoxy group, an aryloxy group, an amido group, an N-alkylcarbamoyl group, an N-alkylsulfamoyl group, an acyloxy group, a carboxy group, a sulfo group, a sulfonamide group, a halogen atom, etc.

Then, practical examples of the couplers which can form organic substrate materials by the reaction with the aforesaid or other developing agents are as follows:

III-1

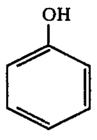

-continued
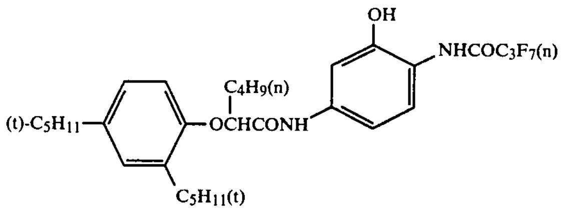
III-2
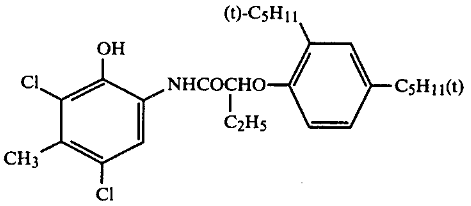
III-3
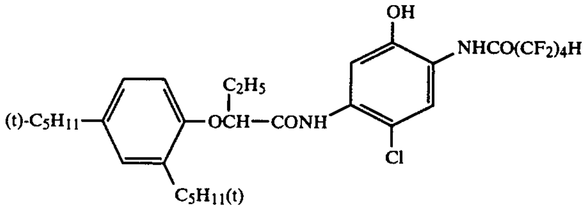
III-4
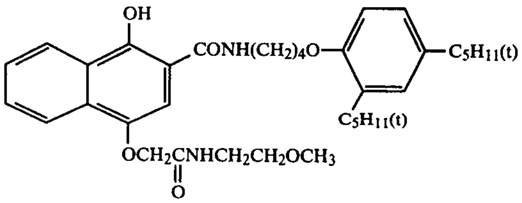
III-5
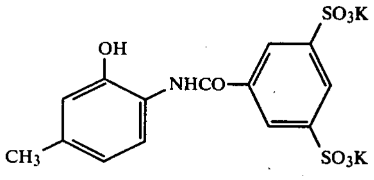
III-6
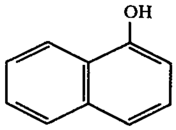
III-7
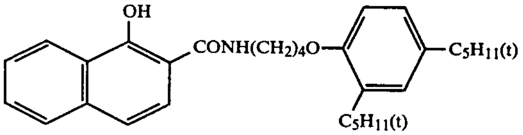
III-8
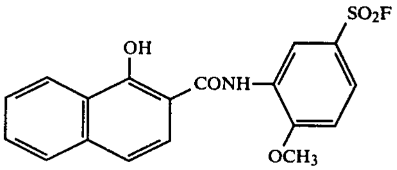
III-9
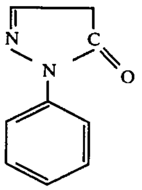
III-10

-continued
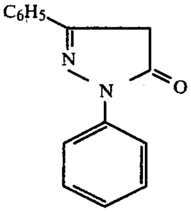
III-11
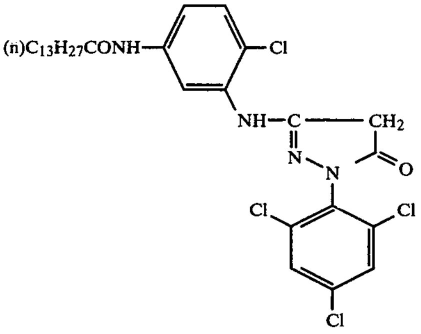
III-12
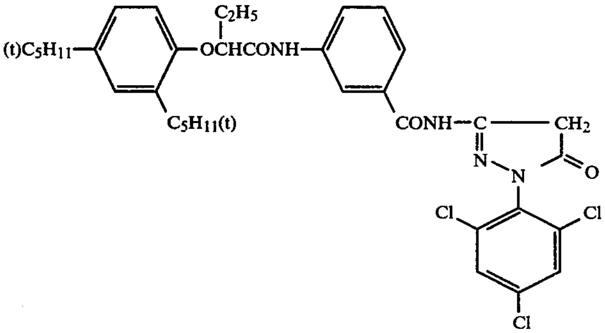
III-13
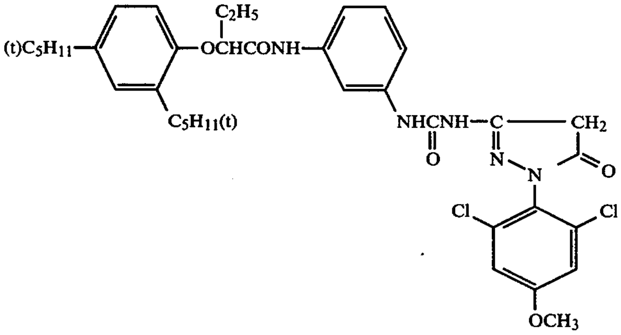
III-14
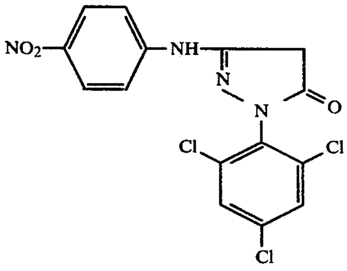
III-15
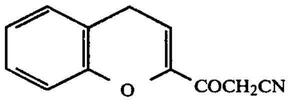
III-16
$CN-CH_2-CN$ III-17

-continued
III-18
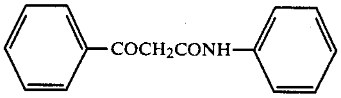
III-19
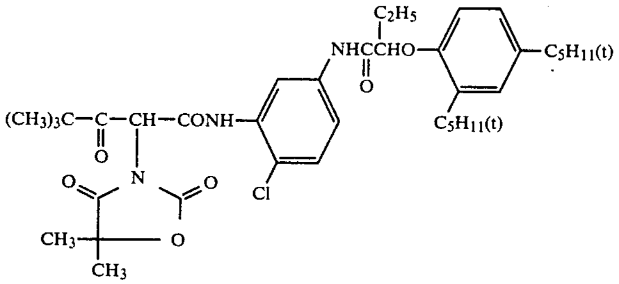
III-20
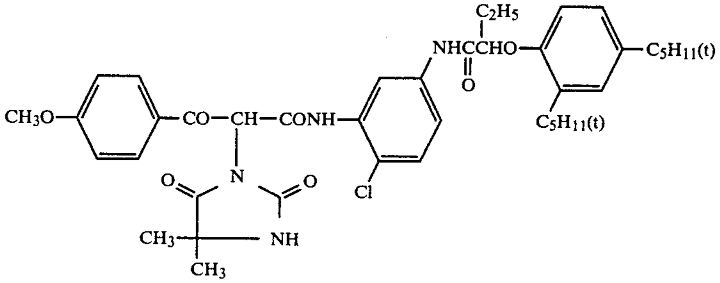
Examples of other dyes used as the organic substrate materials at the practice of this invention are illustrated as follows:
III-21
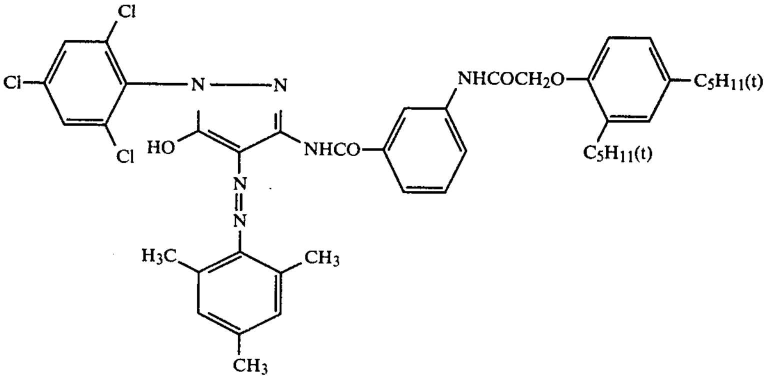
III-22
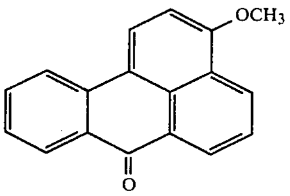
III-23
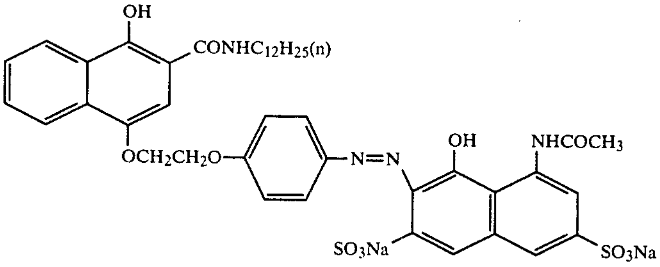

-continued
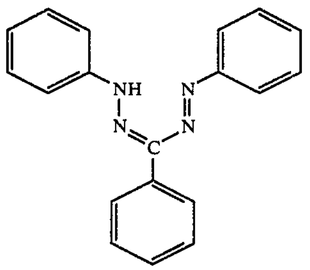
III-24
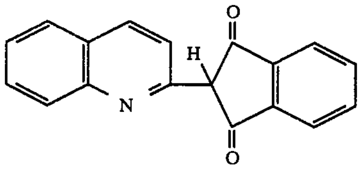
III-25
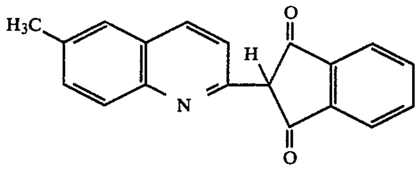
III-26
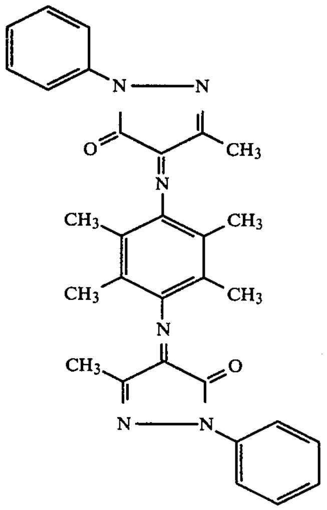
III-27
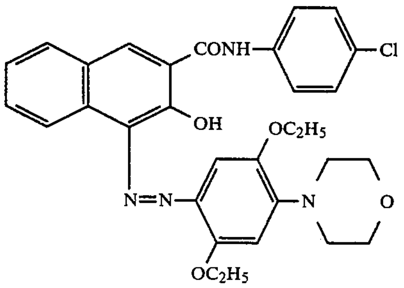
III-28
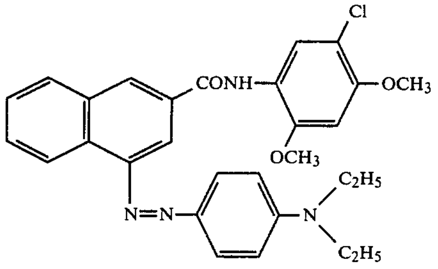
III-29

-continued
III-30
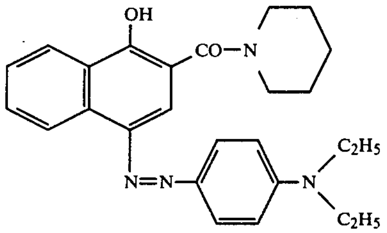
III-31
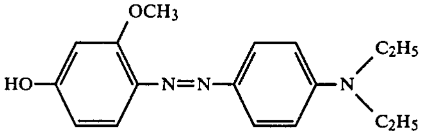
III-32
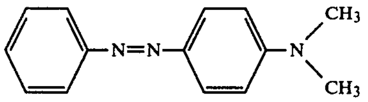
III-33
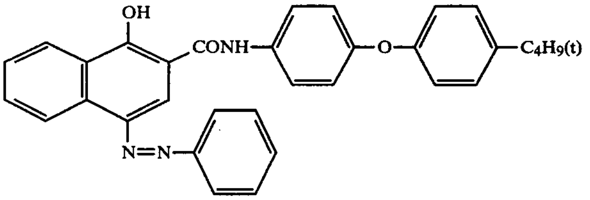
III-34
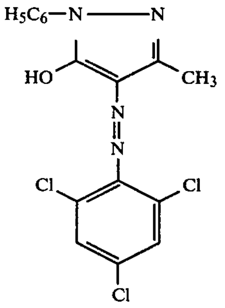
III-35
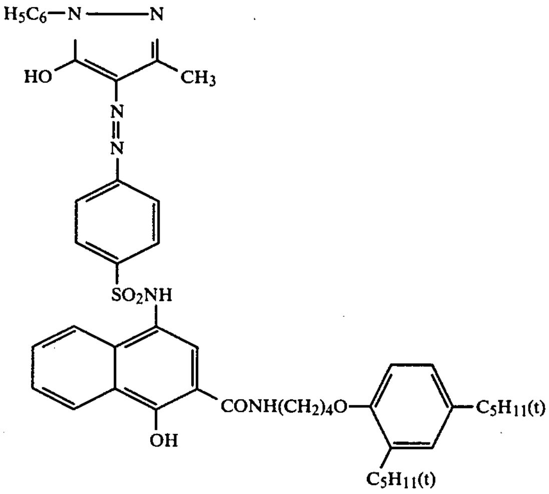
III-36
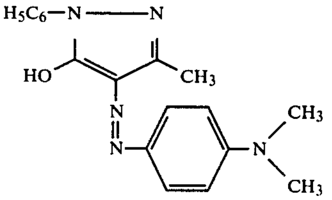

-continued
III-37
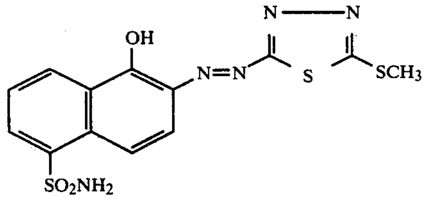
III-38
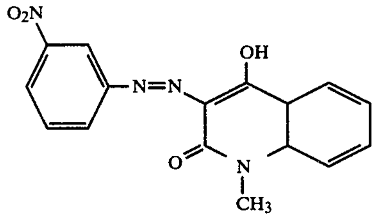
III-39
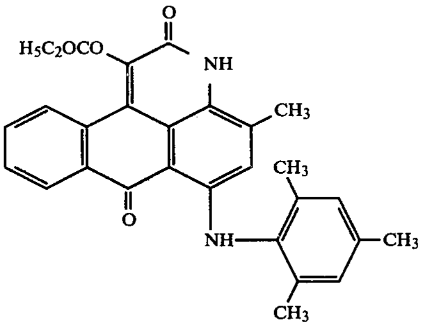
III-40
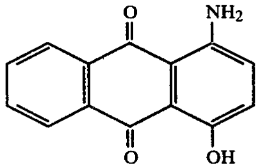
III-41
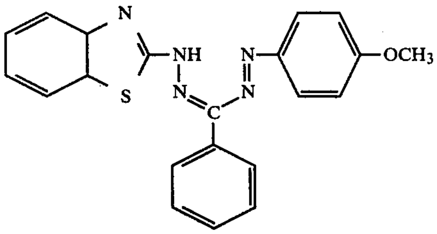
III-42
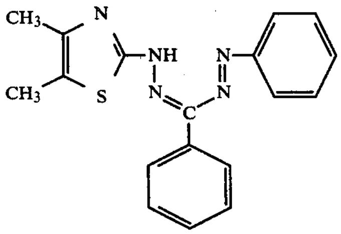
III-43
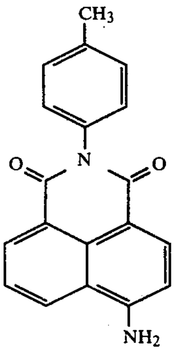

-continued
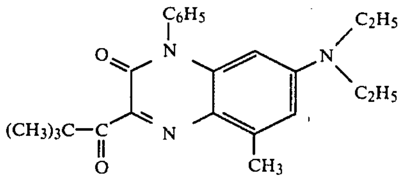
III-44
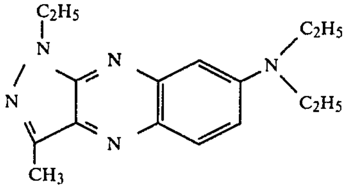
III-45
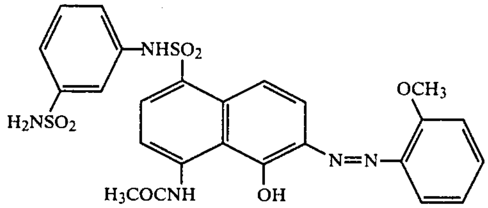
III-46
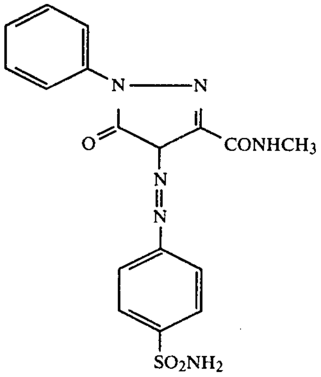
III-47
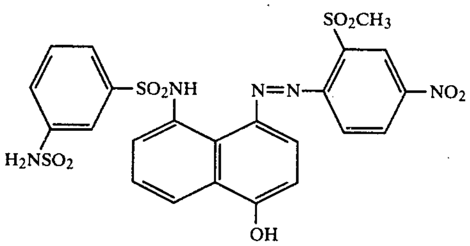
III-48
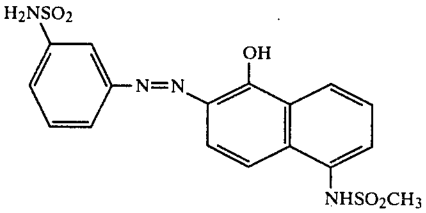
III-49
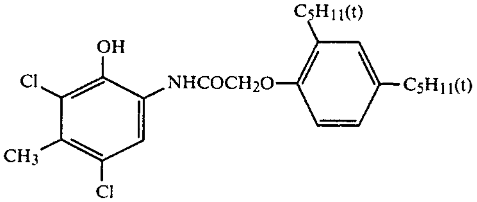
III-50

-continued
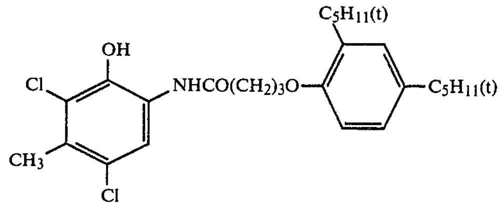
III-51
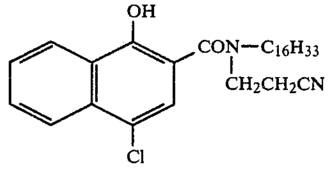
III-52
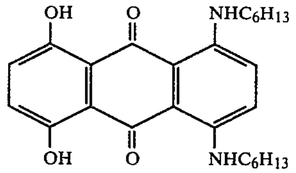
III-53
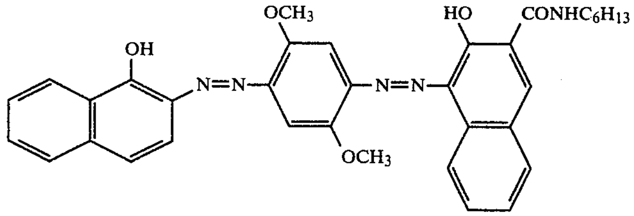
III-54
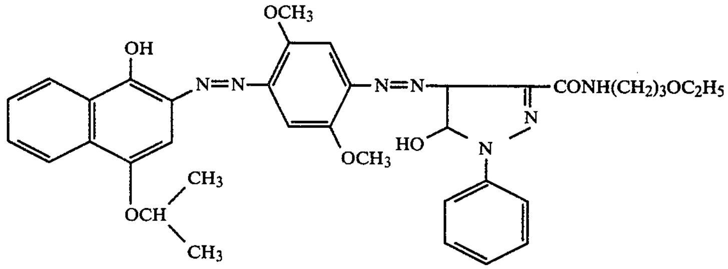
III-55
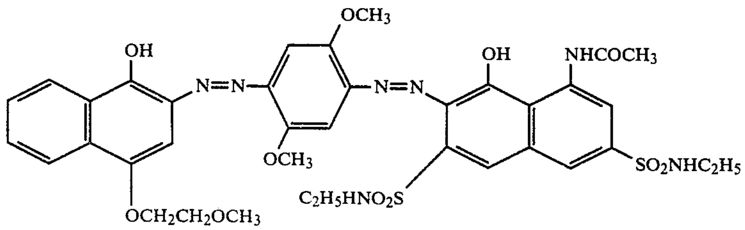
III-56
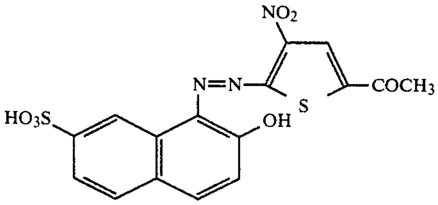
III-57

-continued
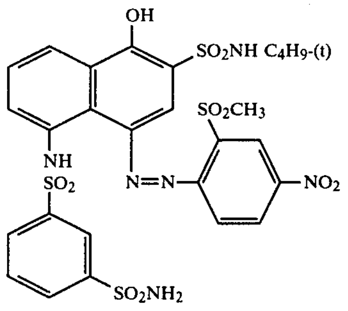
III-58
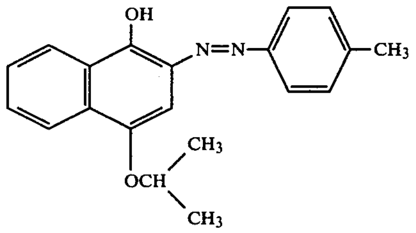
III-59
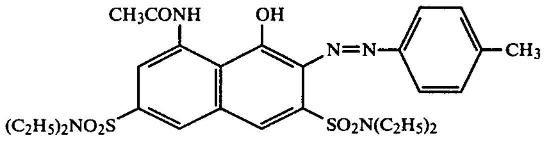
III-60
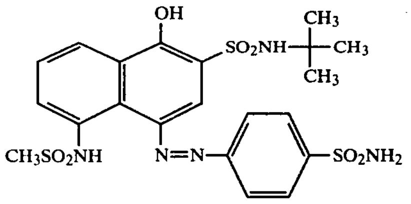
III-61
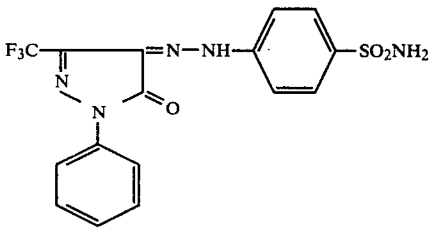
III-62
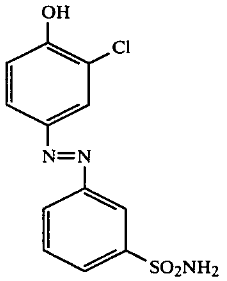
III-63
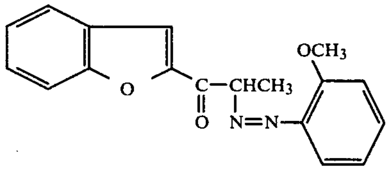
III-64

-continued

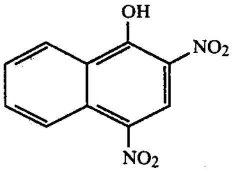

III-65

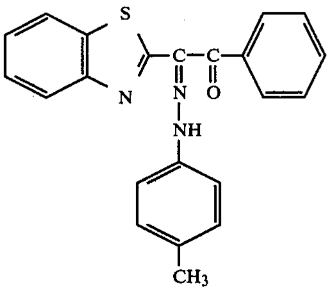

III-66

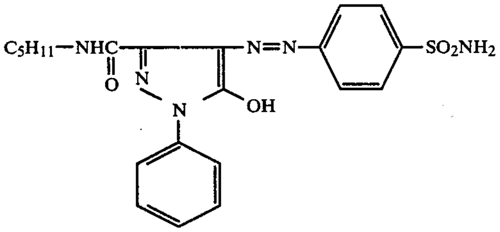

III-67

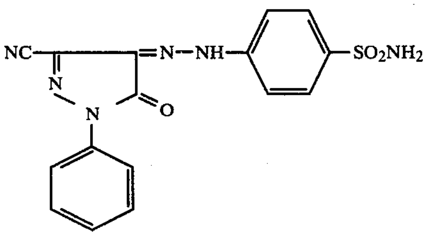

III-68

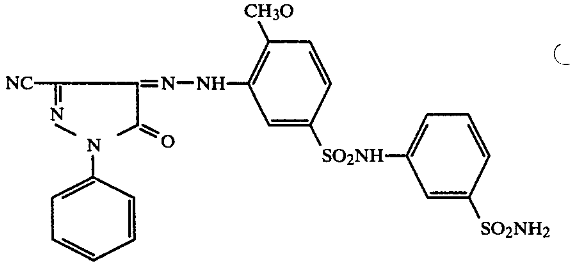

III-69

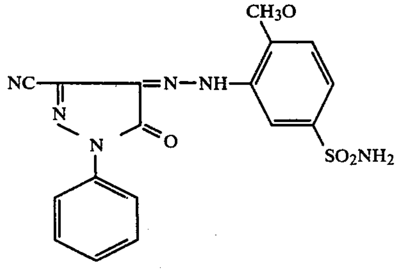

III-70

Other types of dyes perferably used in this invention are the dyes formed by the oxidation of the DRR compounds described in U.S. Publication Application No. 351,673, U.S. Pat. Nos. 3,932,381, 3,928,312, 3,931,144, 3,954,476, 3,929,760, 3,942,987, 3,932,380, 4,013,635, and 4,013,633, Japanese Patent Application (OPI) Nos. 113,624/76, 109,928/76, 104,343/76 and 4819/77. Japanese Patent Application No. 64,533/77 (published as Japanese Patent Application (OPI) 149,328/1978) and Research Disclosure, 86-74 (1976, Nov.) and Research Disclosure No. 13,024 (1975).

Other types of dyes used in this invention are the dyes released by the reaction of an oxidized color developing agent and the DDR couplers as described in British Pat. Nos. 840,731, 904,364, 932,272, 1,014,725, 1,038,331, 1,066,352 and 1,097,064, Japanese Patent Application (OPI) No. 133,021/76, U.S. (U.S. Defensive Publication) No. T900,029, and U.S. Pat. No. 3,227,550.

Still other types of dyes preferably used in this invention are the dye developing agents described in Japanese Patent Publication Nos. 182/57, 18,332/57, 32,130/73, 43,950/71 and 2618/74.

Other types of dyes used in this invention are various dyes used for silver dye bleach process. As yellow dyes used for the purpose, there are azo dyes such as Direct Fast Yellow GC (C.I. 29,000), Chrysophenine (C.I. 24,895), etc.; benzoquinone dyes such as Indigo Golden Yellow IGK (C.I. 59,101), Indigosol Yellow 2GB (C.I. 61,726), Algosol Yellow GCA-CF (C.I. 67,301), Indanthrene Yellow GF (C.I. 68,420), Mikethrene Yellow GC (C.I. 67,300), Indanthrene Yellow GK (C.I. 68,405), etc.; anthraquinone series soluble vat dyes; polycyclic soluble vat dyes; and other vat dyes. As magenta dyes used for the above-mentioned purpose, there are illustrated azo dyes such as Sumilight Supra Rubinol B (C.I. 29,225), Benzo Brilliant Geranine B (C.I. 15,080), etc.; indigoid dyes such as Indigosol Brilliant Pink IR (C.I. 73,361), Indigosol Violet 15R (C.I. 59,321), Indigosol Red Violet IRRL (C.I. 59,316), Indanthrene Red Violet RRK (C.I. 67,895), Mikethrene Brilliant Violet BBK (C.I. 6335), etc.; benzoquinone series soluble vat dyes; anthraquinone series soluble vat dyes; heterocyclic soluble vat dyes; and other vat dyes. As cyan dyes used for the above purpose, there are illustrated azo dyes such as Direct Sky Blue 6B (C.I. 24,410), Direct Brilliant Blue 2B (C.I. 22,610), Sumilight Supra Blue G (C.I. 34,200), etc.; phthalocyanine dyes such as Sumilight Supra Turkish Blue G (C.I. 74,180), Mikethrene Brilliant Blue 4G (C.I. 47,140), etc.; Indanthrene Turkish Blue 5G (C.I. 69,845), Indanthrene Blue GCD (C.I. 73,066), Indigosol 04G (C.I. 73,046), Anthrasol Green (C.I. 59,826), etc.

While the mechanism whereby the complex of the present invention improves light fastness is not entirely clear, it is believed that upon exposure to light the organic substrate (dye image) is excited to a triplet state whereupon the complex interacts with the excited dye to absorb the high energy and thus restore the dye to its original state. Alternatively, oxygen may be excited upon exposure to a singlet state in which case the complex absorbs the high energy of the excited oxygen and restores the oxygen to its original state. In any case the complex of the present invention effectively improves the light fastness of the organic substrate.

As described above, the metal complexes are used in this invention for stabilizing the organic substrate materials. These compounds may be incorporated in one or more silver halide emulsion layers of color photographic materials. Also, these compounds may be incorporated in a layer included in the non-sensitive portion of color photographic transfer materials.

The complexes can be supplied for stabilizing photographic images by incorporation into the hydrophilic colloids constituting the photographic layers of a photographic element. The complexes are incorporated as a solution thereof in an organic solvent having low boiling point or an organic solvent miscible with water which does not adversely influence the photographic properties of the photographic layers, such as, for example, an alcohol (e.g., methanol, ethanol, isopropanol, butanol, etc.), an ether (e.g., dimethyl ether, ethyl methyl ether, diethyl ether, 1-ethoxypropane, etc.) a glycol (e.g. 1,2-ethanediol, 1,2-propanediol, 1,3-propanediol, etc.), a ketone (e.g., acetone, ethyl methyl ketone, 3-pentanone, etc.), an ester (e.g., ethyl formate, methyl acetate, ethyl acetate, etc.), an amide (e.g., formamide, acetamide, succinamide, etc.), and the like. It is desirable that the complex be incorporated before coating, such as when producing silver halide photographic emulsions, when forming an emulsified dispersion of couplers, or when preparing photographic coating compositions.

In order to introduce these complexes into hydrophilic colloids constituting photographic layers, methods usually employed for dispersing couplers in the color photographic fields may be employed. In this regard, U.S. Pat. Nos. 2,304,939 and 2,322,027 disclose the use of high boiling organic solvents for dissolving these materials. Other applicable methods are described in U.S. Pat. Nos. 2,801,170, 2,801,171 and 2,949,360, wherein low boiling or water-soluble organic solvents are used together with high boiling organic solvents.

Examples of the high boiling organic solvents which are effective for dispersing the substrate material and metal complexes in this invention are di-n-butyl phthalate, benzyl phthalate, triphenyl phosphate, tri-o-cresyl phosphate, diphenylmono-p-pert-butylphenyl phosphate, monophenyl-di-p-tert-butylphenyl phoshpate, diphenyl-mono-o-chlorophenyl phosphate, monophenyl-di-o-chlorophenyl phosphate, 2,4-di-n-amylphenol, 2,4-di-t-amylphenol, N,N-diethyllaurylamide as well as trioctyl phosphate and trihexyl phosphate described in U.S. Pat. No. 3,676,137.

The low boiling or water-soluble organic solvents which can be advantageously used together with these high boiling organic solvents are disclosed in, for example, U.S. Pat. Nos. 2,801,171, 2,801,170 and 2,949,360.

These organic solvents include:

(1) low boiling organic solvents substantially immiscible in water, such as, for example, methyl acetate, ethyl acetate, propyl acetate, butyl acetate, isopropyl acetate, ethyl propionate, sec-butyl alcohol, ethyl formate, nitromethane, nitroethane, carbon tetrachloride, chloroform, etc., and (2) water-miscible organic solvents such as, for example, methyl isobutyl ketone, β-ethoxyethyl acetate, β-butoxytetrahydrofurfuryl adipate, diethylene glycol monoacetate, methoxytriglycol acetate, acetonylacetone, diacetone alcohol, ethylene glycol, acetone, methanol, ethanol, acetonitrile, dimethylformamide, dioxane, etc.

In general, the complex of the formula (I) is dissolved or suspended in an appropriate solvent which is chosen depending upon the physical properties of the complex used from water, water-miscible and water-immiscible organic and inorganic solvents (the details of which are described in U.S. Pat. No. 3,966,468) and the organic substrate material is dissolved or suspended therein. Alternatively, again depending upon the physical properties of the compounds, solutions and/or dispersions may be prepared separately and subsequently mixed. For example, a fluorescent whitening agent may be dissolved or suspended in an organic or inorganic solvent such as water or dimethyl formamide, etc., together with the complex of the present invention or separately; and the mixture may be coated onto or incorporated into a suitable base substance. An adjacent double layer coating is possible and in some cases may be preferred if some diffusion between the contiguous layers occurs and light fastness improvement is effected. Where it is desired to improve the light fastness in a colored polymer for use of agricultural vinyl sheets, the colored polymer and complex of the formula (I) are likewise mixed in the form of a solution, dispersion, etc., followed by extrusion molding, etc., in a conventional manner.

The colored polymer as used herein is a polymer containing a coloring material in a state of molecular dispersion or melt. The polymer is represented by natural resins other than gelatin, e.g., cellulose and derivatives thereof, vinyl resins, polycondensates, silicone resins, alkyd resins, polyamides, paraffin and mineral waxes as described in U.S. Pat. No. 3,966,468.

In the case of a photographic material, the substrate material (the dye image) and the complex each may be present in one or more of the hydrophilic colloid layers making up the photographic element (film, paper, diffusion transfer unit, etc.). It is preferred that the metal chelate complex and the organic substrate material be present (i.e., co-exist) in the same emulsion layer, of course, the effects of the present invention can also be accomplished when the complex and substrate are present in contiguous layers as long as diffusion is allowed to occur between the layers. Were any (further) undesirable diffusion to occur, conventional mordanting techniques could be applied to the present invention. In the case of incorporating the complex into a silver halide emulsion layer, the complex can be incorporated into each emulsion layer making up the photographic element. In this case, the total amount of complex is present in the amounts set forth above. The complex and substrate may be present in non-light sensitive elements or layers as well, such as the dye image-receiving layer used in diffusion transfer film units. In the case of image transfer units, the metal chelate complex is preferably located in a layer where dye images are finally found, i.e., in an image-receiving layer. Usually, the dye images formed in the image-receiving layer do not diffuse further into any other layer(s) so that the complex is easily maintained in the vicinity of the dye. When the organic substrate material and the complex are incorporated in such a non-photosensitive image-recording or image-receiving element, it is preferred that these materials have been mordanted. Therefore, in the case of using these materials in the aforesaid manner, it is preferred that the complex contain a ligand capable of retaining it in the mordant layer of the image-receiving element so that the complex does not diffuse away from the dye to be stabilized thereby.

A number of types of image transfer film units are particularly appropriate for the practice of the present invention. One is the imbibition transfer film unit set forth in U.S. Pat. No. 2,882,156. The present invention can be further used in conjunction with the color image transfer film unit described in U.S. Pat. Nos. 2,087,817, 3,185,567, 2,983,606, 3,253,915, 3,227,550, 3,227,551, 3,227,552, 3,415,646, 3,594,164 and 3,594,165 and Belgian Pat. Nos. 757,959 and 757,960.

The organic substrate materials and the complexes at the practice of this invention can be used together with the materials as described in *Product Licensing Index*, Vol. 92, No. 9232, 107-110 (1971, December) according to the manner as described therein.

Any amount of the complex will bring about some improvement in the light fastness of the organic substrate and theoretically there is no upper limit for the amount of the complex. Preferably, the complex is present in an amount of at least 0.1 mol% based on 1 mol of the organic substrate material, more preferably in an amount of 0.1 to 1,000 mol%, and most preferably in an amount of 1 to 300 mol%. In the case of a photographic material, the amount is often expressed in a weight unit per square meter of photographic material which can be calculated from the parameters set out above. For convenience, however, in the case of a photographic material, the complex is preferably present in an amount of at least 1 micromole per square meter of the photographic material, and more preferably in an amount of from about 10 to $1\times10^4$ micromoles per square meter of the material. The concentration of the substrate material corresponds in general to that for the image forming material usually adopted in color photographic technology. As is well known to those skilled in the art, the substrate material is preferably present in the range from about 10 to $10^4$ micromoles per square meter of the photographic material. A more preferable range is from about 100 to about $3\times10^3$ micromoles pre square meter of the photographic product.

The organic substrate material used in this invention generally has a maximum absorption peak in the wavelength region less than about 800 nm. However, the organic substrate material having the maximum absorption peak in the region of from about 300 nm to about 800 nm is preferred and the organic substrate material having the maximum absorption peak in the range of from about 400 nm to about 800 nm is most preferred.

In photographic materials based on this invention, any material ordinarily used as the supports for photographic materials may be used as the support therefor in this invention. Examples thereof are cellulose nitrate films, cellulose acetate films, cellulose acetate butyrate films, cellulose acetate propionate films, polystyrene films, polyethylene terephthalate films, polycarbonate films, laminaed sheets of these films, and papers. Also, baryta-coated papers, papers coated with α-olefin polymer in particular, a polymer of an α-olefin having 2 to 10 carbon atoms, such as polyethylene, polypropylene, etc., and plastic films the surface of which have been roughened to improve their adhesion to other polymers as shown in Japanese Patent Publication No. 19,068/72 are preferably used as the supports for photographic materials.

In photographic materials used in the method of this invention, various hydrophilic colloids are used. Examples of the hydrophilic colloids used as the binders for photographic silver halide emulsions and/or other coating compositions for photographic layers are gelatin; colloidal albumin; casein; cellulose derivatives such as carboxymethyl cellulose, hyroxyethyl cellulose; etc.; sugar derivatives such as agar agar, sodium alginate, starch derivatives, etc.; synthetic hydrophilic colloids such as polyvinyl alcohol, poly-N-vinylpyrrolidone, polyacrylic acid copolymers, maleic anhydride copolymers, polyacrylamide, and the derivatives or partially hydrolyzed products thereof. If necessary, a mixture of two or more of these colloids which are compatible with each other may be used.

Among the aforesaid materials, gelatin is most generally used but gelatin may be replaced partially or wholly with a synthetic polymer. Furthermore, so-called gelatin derivatives, that is, gelatin modified by treatment with an amino group, an imino group, a hydroxy group, a carboxy group, etc., contained in the gelatin molecule as a functional group with a reagent having a functional group which can react with these groups or graft gelatin having bonded thereto the molecular chain of another polymer may be used in place of gelatin.

The silver halide photographic emulsion layers or other photographic layers of photographic materials used in this invention may further contain synthetic polymers such as, for example, water-dispersed vinyl polymers in the form of a latex, in particular, a compound or compounds capable of increasing the dimensional stability of the photographic materials solely or together with a hydrophilic water-permeable colloid.

The silver halide photographic emulsion used in the method of this invention is usually prepared by mixing an aqueous solution of a water-soluble silver salt (e.g., silver nitrate) and an aqueous solution of a water-soluble halogen salt (e.g., potassium bromide) in the presence of a water-soluble polymer solution such as an aqueous solution of gelatin. As such as silver halide, there is silver chloride, silver bromide as well as mixed silver halides such as silver chlorobromide, silver chloroiodide, silver chloroiodobromide, etc. These silver halide grains may be prepared according to a known or conventional processes. As a matter of course, they may be advantageously prepared using the so-called single jet method or double jet method or the controlled double jet method. Also, two or more different silver halide emulsions prepared separately may be used in mixture.

The above-mentioned silver halide photographic emulsions may further contain various compounds for preventing a reduction in sensitivity and the formation of fog during production, preservation or processing of the photographic material. As examples of such compounds, there are 4-hydroxy-6-methyl-1,3,3a,7-tetrazaindene, 3-methylbenzothiazole, 1-phenyl-5-mercaptotetrazole as well as many heterocyclic compounds, mercury-containing compounds, mercapto compounds, metal salts, etc.

The silver halide emulsions used in this invention may also be chemically sensitized in a conventional manner. As examples of chemical sensitizers used for the purpose, there are gold compounds such as an aurichlorate, gold trichloride, etc.; salts of noble metals such as platinum, palladium, iridium, and rhodium; sulfur compounds capable of forming silver sulfide by causing reaction with a silver salt, such as sodium thiosulfate, etc.; stannous salts, amines; and other reducing materials.

The silver halide photographic emulsions used in this invention may, if necessary, be subjected to a spectral sensitization or super dye sensitization using cyanine dyes such as cyanine, merocyanine, carbocyanine, etc., solely or as a combination thereof or using a combination of the cyanine dye or dyes and styryl dyes. These days are properly selected according to the objects and use of the photographic materials, such as the wavelength region and sensitivity to be sensitized.

The hydrophilic colloid layers of photographic materials used in the method of this invention can be, if necessary, hardened by various cross-linking agents; for example, aldehyde series compounds, active halogen compounds, vinylsulfone compounds, carbodiimide compounds, N-methylol compounds, epoxy compounds, etc.

In applying the method of this invention to color photographic materials, after image exposure, the color photographic material may be processed in a conventional manner to form color images. The main processing steps in such case are color development, bleach, and fix and, if necessary, other steps such as washing and stabilization. In these steps, two or more steps may be performed in one step as blix step. The color development is usually performed in an alkaline solution containing an aromatic primary amino developing agent. Preferred examples of the aromatic primary amino developing agent are the compounds shown by formulae (A) to (L) described above.

In applying the method of this invention to color photographic materials, wherein the color photographic material is a color photographic diffusion transfer film unit, the processing of the photographic material is carried out automatically in the photographic material. In this case, a color developer containing a color developing agent is contained in a rupturable container. As the developing agent, N-methylaminophenol, 1-phenyl-3-pyrazolidone, 1-phenyl-4,4-dimethyl-3-pyrazolidone, 1-phenyl-4-methylhydroxymethyl-3-pyrazolidone, 3-methoxy-N,N-diethyl-p-phenylenediamine, etc., in addition to the compounds shown by formulae (A) to (L) above are suitable.

For forming color images in photographic materials based on this invention, various known methods can be used, such as the coupling reaction of the above-described dye-forming color couplers and the oxidation product of a p-phenylenediamine series color developing agent; development with a dye developers; the oxidation cleavage reaction of DRR compounds; the dye-releasing reaction upon coupling of DDR couplers; the dye-forming reaction upon coupling reaction of DDR couplers and a silver dye bleaching process.

Accordingly, this invention can be applied to various kinds of color photographic materials such as color positive films, color papers, color negative films, color reversal films, color diffusion transfer film units, silver dye bleaching photographic materials, etc.

The following examples are provided for further understanding of the method of this invention. They are not to be construed as limiting.

EXAMPLE 1

In a mixture of 3 ml of tricresyl phosphate and 5 ml of ethyl acetate was dissolved 0.1 g of 1-(2,4,6-trichlorophenyl)-3-(2-chloro-5-tetradecanamido)anilino-4-[4-(N-ethyl-N-$\beta$-methanesulfonamidoethyl)amino-phenylimino]-5-oxo-2-pyrazoline and the solution was dispersed by emulsification in 10 g of an aqueous 10% gelatin solution containing 1 ml of an aqueous solution of 1% sodium dodecylbenzenesulfonate. Then, the emulsified dispersion was mixed with 10 g of an aqueous 10% gelatin solution and the mixture was coated on a paper support of which the both surfaces were coated with polyethylene, and dired to provide Sample A.

By following the same procedure as in preparing Sample A but adding 18 mg of Compound I-5 of this invention, Sample B was prepared. Also, by following the same procedure as above but adding 20 mg or 200 mg of 2,5-di-tert-octylhydroquinone (a known light fading preventing agent for dyes), Samples C and D were respectively prepared. The coverage of the dye was 60 mg/m$^2$ in each sample. The coverage of the fade preventing agent was 10.8 mg/m$^2$ in Sample B, 12 mg/m$^2$ in Sample C and 120 mg/m$^2$ in Sample D. Samples A to D thus-prepared were subjected to a fading test for 36 hours using a xenon tester (200,000 lux) while applying thereto Ultraviolet Cut Filter C-40 made by the Fuji Photo Film Co., Ltd. The results are shown in the following table.

TABLE I

| | Initial Density | Density after 36 Hours |
|---|---|---|
| Sample A | 0.79 | 0.03 |

TABLE I-continued

| | Initial Density | Density after 36 Hours |
|---|---|---|
| Sample B | 0.81 | 0.73 |
| Sample C | 0.81 | 0.09 |
| Sample D | 0.82 | 0.38 |

The density in the table was measured by means of Macbeth densitometer RD 514 using a green filter of Status AA Filter. As shown in the above table, Sample B containing Compound I-5 of this invention was very low in fading as compared with Samples A, C and D and, in particular, in spite of the fact that Sample C and Sample D contained 2,5-di-tert-octylhydroquinone in an amount equivalent to or 10 mole times the amount of compound I-5 in Sample B, fading of these comparison samples were severe as compared with Sample B, which shows that compound I-5 of this invention has an astonishing effect for preventing light fading of dyes.

EXAMPLE 2

In a mixture of 3 ml of dibutyl phthalate and 5 ml of ethyl acetate was dissolved 0.1 g of the dye having the following structure

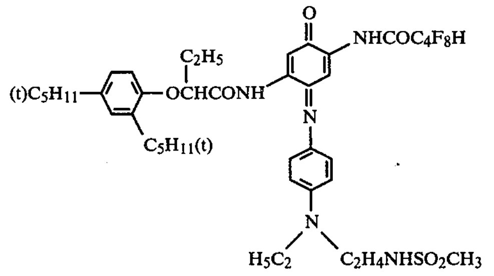

and the solution was dispersed by emulsification in 10 g of an aqueous 10% gelatin solution containing 1 ml of an aqueous solution of 1% sodium dodecylbenzenesulfonate.

Then, the emulsified dispersion was mixed with 10 g of an aqueous 10% gelatin solution and the mixture was coated on a paper support the both surfaces of which had been coated with polyethylene and dried to provide Sample E.

Also, by following the above procedure but adding 25 mg of compound II-5 of this invention to the emulsified dispersion at the time of preparing the dispersion, Sample F was prepared. By following the same procedure but adding 100 mg of α-tocopherol as a known light fading preventing agent, Sample G was prepared. The coverage of the dye was 50 mg/m$^2$ in each sample. In Sample F, compound II-5 was coated in an amount of 12.5 mg/m$^2$ and in Sample G, α-tocopherol was coated in an amount of 50 mg/m$^2$. With each Samples E to G, a fading test was performed for 48 hours by means of a xenon tester of 200,000 lux using Ultraviolet Cut Filter C-40 made by the Fuji Photo Film Co., Ltd. The results are shown in Table II. The optical density in the table is the value measured by means of Macbeth densitometer RD 514 using a red filter of Status AA Filter.

TABLE II

| | Initial Density | Density after Fading |
|---|---|---|
| Sample E | 0.90 | 0.20 |
| Sample F | 0.91 | 0.50 |
| Sample G | 0.90 | 0.26 |

As shown in the above table, Sample F containing compound II-5 of this invention showed excellent light fading preventing effect. It is also noted that compounds which effectively prevent light fading for cyan dyes have not yet been known but it has now been confirmed that the compound of this invention is very effective for cyan dyes.

EXAMPLE 3

In a mixture of 30 ml of trioctyl phosphate, 5 ml of dimethylformamide and 15 ml of ethyl acetate was dissolved 10 g of a magenta coupler, 1-(2,4,6-trichlorophenyl)-3-[(2-chloro-5-tetradecanamido)anilino]-2-pyrazoline-5-one and the solution was dispersed by emulsification in 80 g of an aqueous 10% gelatin solution containing 8 ml of an aqueous solution of 1% sodium dodecylbenzenesulfonate.

Then, the emulsified dispersion was mixed with 145 g (7 g as Ag) of a green-sensitive silver chlorobromide emulsion (50 mol% Br) and after adding thereto 3 ml of an aqueous solution of 1% sodium dodecylbenzenesulfonate as a coating aid, the resulting mixture was coated on a paper support the bath surfaces of which had been coated with polyethylene and dried to provide Sample H. The coverage of the coupler was 400 mg/m$^2$.

By following the above precedure but adding 1.6 g of compound II-7 of this invention to the emulsified dispersion at the time of preparing the emulsified dispersion, Sample I was prepared and further by following above procedure but adding 1.1 g of 2,2'-methylenebis(4-methyl-6-tert-butylphenol) (a known light fading preventing agent for dyes), Sample J was prepared. In Sample I, compound II-7 was coated in an amount of 64 mg/m$^2$ and in Sample J the fade preventing agent was coated in 44 mg/m$^2$.

The samples were exposed for 1 second under 1,000 lux and processed by the following processing compositions:

| | |
|---|---|
| Developer: | |
| Benzyl Alcohol | 15 ml |
| Diethylenetriamine Pentaacetate | 5 g |
| KBr | 0.4 g |
| $Na_2SO_3$ | 5 g |
| $Na_2CO_3$ | 30 g |
| Hydroxylamine Sulfate | 2 g |
| 4-Amino-3-methyl-N-ethyl-N-β-(methane-sulfonamido)ethylaniline . $3/2H_2SO_3$ . $H_2O$ | 4.5 g |
| Water to make | 1 l |
| pH | 10.1 |
| Blix Solution: | |
| Ammonium Thiosulfate (70 wt %) | 150 ml |
| $Na_2SO_3$ | 5 g |
| Na[Fe(EDTA)] | 40 g |
| EDTA | 4 g |
| Water to make | 1 l |
| pH | 6.8 |

| Processing Step | Temperature | Time |
|---|---|---|
| Development | 33° C. | 3 min 30 sec |
| Blixing | 33° C. | 1 min 30 sec |
| Washing | 28-35° C. | 3 min |

Each sample having the color images thus-formed was subjected to a fading test for 4 weeks by means of a fluorescent lamp fade-o-meter (20,000 lux) using Ultraviolet Absorption Filter C-40 made by the Fuji Photo Film Co., Ltd. for cutting the light of wavelengths shorter than 400 nm. The results are shown in Table III. The density was measured by means of Macbeth densitometer RD-514 using Status AA Filter and the density change at the portion having the initial density of 2.0 waw measured.

TABLE III

| | Density of the Portion Having Initial Density of 2.0 by the Fading Test | Dye* Remnant |
|---|---|---|
| Sample H | 0.48 | 24% |
| Sample I | 1.73 | 86.5% |
| Sample J | 1.08 | 54.0% |

*Dye Remnant = (density after fading/2.0) × 100

The results show that compound II-7 of this invention is also an effective fading preventing agent.

EXAMPLE 4

A solution of 15 mg of a dye having the structure below and 500 mg of polycarbonate, Lexan 145 (trade name, manufactured by General Electric Co., Ltd.) in 100 ml of dichloromethane was coated onto a glass plate using a spinner. A magenta-colored film of 5.5μ thickness was thus-prepared as Sample K.

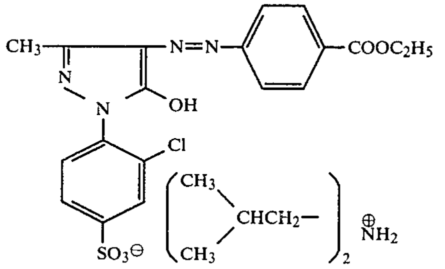

In a similar manner, five kinds of colored films were prepared as Samples L, M, N, O and P except that Compounds II-2, II-21, II-22, II-23 and II-24 were further incorporated into the solution, respectively.

The coating rate of the dye and the fade prevention compounds were 500 mg/m$^2$ and 50 mg/m$^2$, respectively.

The thus-obtained films were exposed to sunlight for 1 month and a color fading test was carried out. The results obtained are shown in Table IV below, in which density was measured at 450 nm.

TABLE IV

| Sample | Initial Density | Density after Fading |
|---|---|---|
| K | 1.50 | 0.50 |
| L | 1.50 | 1.05 |
| M | 1.50 | 0.95 |
| N | 1.50 | 0.85 |
| O | 1.50 | 0.95 |
| P | 1.50 | 0.80 |

As is clearly seen from the results above, the samples containing the compounds of the present invention provide excellent fade prevention effect, in particular, the effect is remarkable when Ni, Cu or Co is used as a ligand for the chelate complexes.

Briefly summarizing the effects achieved by the metal chelate complex employed in the present invention:

(1) The metal chelate complex is readily soluble in organic solvents.

(2) In addition, the structure of the chelate complex can easily be modified so that it permits a large latitude for obtaining desired solubility.

(3) As a result of the latitude of its solubility, the complex is readily enveloped in oil droplets and, as a result, photographically undesired interaction with silver halide (e.g., desensitization) is avoidable.

(4) Due to its extremely high solubility, a small amount of the complex is sufficient to effect light fastness; conversely, a large amount can also be employed as in the case of umbrellas, agricultural vinyl cover sheets, etc.

(5) Where the chelate is used in a photographic element, no adverse effect on photographic properties is encountered.

(6) The complex is the first fading prevention agent suitable for improving the light fastness of cyan dye images.

For the reasons above, the metal chelate complex used in the present invention provides excellent light fastness.

While the invention has been described in detail and with reference to specific embodiments thereof, it will be apparent to one skilled in the art that various changes and modifications can be made therein without departing from the spirit and scope thereof.

What is claimed is:

1. An element stabilized against the action of light comprising the combination of (a) a non-uniform photographic dye image, said dye of said dye image having an absorption maximum in the wavelength range between about 300 nm and about 800 nm, and (b) at least one of the complexes represented by the general formula (I) or (II):

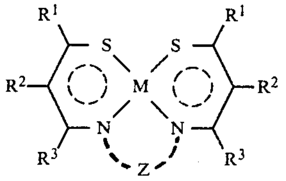

(I)

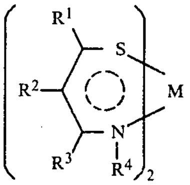

(II)

wherein M represents a Cu, Co, Ni, Pd or Pt atom; $R^1$ and $R^4$, which may be the same or different, each represents an alkyl group or an aryl group; $R^2$ and $R^3$, which may be the same or different, each represents a hydrogen atom, an alkyl group or an aryl group; or $R^1$ and $R^2$, and $R^3$ and $R^4$ combine with each other and represent a non-metallic atomic group necessary for forming a 6-membered ring; and Z represents the non-metallic atomic group necessary to complete a 5-membered ring, a 6-membered ring, an 8-membered ring, or a 10-membered ring.

2. The element as claimed in claim 1, wherein said dye is at least one of an anthraquinone dye, a quinoneimine dye, an azo dye, a methine dye, a polymethine dye, an indoamine dye, an indophenol dye and a formazan dye.

3. The element as claimed in claim 1, wherein said dye is the dye image formed from a dye-forming coupler, a DDR coupler, a DRR compound, a dye developer, or a dye for a silver dye bleaching process.

4. The element as claimed in claim 1, wherein said complexes represented by the general formula (I) or (II) are those represented by the following general formula (I-A) or (II-A), respectively

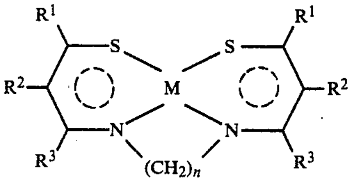
(I-A)

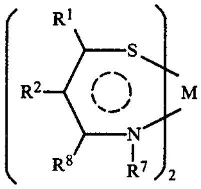
(II-A)

wherein M represents a Cu, Co, Ni, Pd or Pt atom; $R^1$ and $R^7$ each represents an alkyl group or an aryl group; $R^2$, $R^3$ and $R^8$ each represents a hydrogen atom, an alkyl group or an aryl group; $R^1$ and $R^2$ may combine with one another to represent the non-metallic atomic group necessary to form a 6-membered ring; and n represents 2 or 3.

5. The element as claimed in claim 3, wherein said dye-forming coupler is a yellow dye-forming coupler selected from benzoylacetanilide and α-pivaylacetanilide couplers; a magenta dye-forming coupler selected from 5-pyrazolone, indazolone, pyrazolinobenzimidazole, pyrazolo-s-triazole, and cyanoacetylcumarone couplers; or a cyan dye-forming coupler selected from phenol and naphthol couplers.

6. The element as claimed in claim 4, where in the complexes represented by the general formula (I-A) or (II-A), M is a Cu, Co or Ni atom.

7. A color photographic material comprising at least one layer containing a non-uniform photographic dye image, said dye of said dye image having an absorption maximum in the wavelength range between about 300 nm and about 800 nm, wherein said layer or an adjacent layer thereto contains at least one of the complexes represented by the general formula (I) or (II)

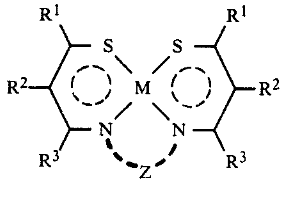
(I)

-continued

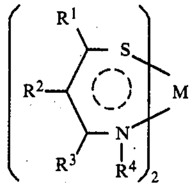
(II)

wherein M represents a Cu, Co, Ni, Pd or Pt atom; $R^1$ and $R^4$, which may be the same or different, each represents an alkyl group or an aryl group; $R^2$ and $R^3$, which may be the same or different, each represents a hydrogen atom, an alkyl group or an aryl group; or $R^1$ and $R^2$, and $R^3$ and $R^4$ combine with each other and represent a non-metallic atomic group necessary for forming a 6-membered ring; and Z represents the non-metallic atomic group necessary to complete a 5-membered ring, a 6-membered ring, an 8-membered ring, or a 10-membered ring, stabilizing said dye to the action of light.

8. The color photographic material of claim 7, wherein said photographic dye image is formed from a color coupler, a DDR coupler, a DRR compound, a dye developer, or as a result of a silver dye bleaching process.

9. The photographic material of claim 8, wherein said dye is formed by the reaction of a primary aromatic amine color developing agent and a cyan, magenta or yellow dye image forming coupler.

10. The photographic material of claim 7, wherein said complexes represented by the general formula (I) or (II) are those represented by the general formula (I-A) or (II-A), respectively

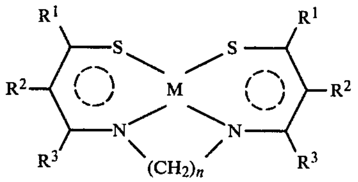
(I-A)

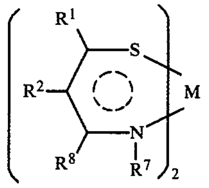
(II-A)

wherein M represents a Cu, Co, Ni, Pd or Pt atom; $R^1$ and $R^7$ each represents an alkyl group or an aryl group; $R^2$, $R^3$ and $R^8$ each represents a hydrogen atom, an alkyl group or an aryl group; $R^1$ and $R^2$ may combine with one another and represent the non-metallic atomic group necessary to form a 6-membered ring; and n represents 2 or 3.

11. The photographic material of claim 9, wherein said dye image forming coupler is a yellow dye-forming coupler selected from the group consisting of benzoylacetanilide and a-pivalylacetanilide couplers, a magenta dye-forming coupler selected from the group consisting of 5-pyrazolone, indazolone, pyrazolinebenzimidazole, pyrazolo-s-triazole, and cyanoacetylcumarone couplers; or a cyan dye-forming coupler selected from the group consisting of phenol and naphthol couplers.

12. The photographic material of claim 10, where in the complexes represented by the general formula (I-A) or (II-A) M is a Cu, Co or Ni atom.

13. The photographic material of claim 7, wherein said photographic dye image is composed of at least one of an anthraquinone dye, a quinoneimine dye, an azo dye, a methine dye, a polymethine dye, an indoamine dye, an indophenol dye and a formazan dye.

14. The element of claim 1, wherein said element is a photographic layer or layers, or a photographic material.

15. The element of claim 14, wherein said element is a photographic material and wherein said combination of said dye and said at least one of the complexes represented by the formula (I) or (II) is incorporated into at least one layer selected from the group consisting of one or more hydrophilic colloid layers and one or more photographic emulsion layers in said photographic material.

16. The element of claim 15, wherein said compexes represented by the formula (I) or (II) and said dye are incorporated into separate layers but layers contiguous thereto or are incorporated as a combination in the same layer.

* * * * *